(12) United States Patent
Osorio et al.

(10) Patent No.: US 10,980,851 B2
(45) Date of Patent: Apr. 20, 2021

(54) **TOPICAL SKINCARE COMPOSITIONS COMPRISING *CENTELLA ASIATICA* SELECTED TRITERPENES**

(71) Applicant: The Procter & Gamble Company, Cincinnati, OH (US)

(72) Inventors: Karen Marie Osorio, Cincinnati, OH (US); Janette Villalobos Lingoes, Cincinnati, OH (US); Debbie Lynn Hartsell, Cincinnati, OH (US); Kim Lynn Webb, Fairfield, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

(21) Appl. No.: 16/003,875

(22) Filed: Jun. 8, 2018

(65) Prior Publication Data
US 2019/0374591 A1 Dec. 12, 2019

(51) Int. Cl.
| | |
|---|---|
| *A61K 36/899* | (2006.01) |
| *A61K 36/23* | (2006.01) |
| *A61K 36/00* | (2006.01) |
| *A61P 17/06* | (2006.01) |
| *A61P 17/04* | (2006.01) |
| *A61K 9/00* | (2006.01) |
| *A61K 31/164* | (2006.01) |

(52) U.S. Cl.
CPC ............ *A61K 36/23* (2013.01); *A61K 9/0014* (2013.01); *A61K 31/164* (2013.01); *A61K 36/899* (2013.01); *A61P 17/04* (2018.01); *A61P 17/06* (2018.01)

(58) Field of Classification Search
None
See application file for complete search history.

(56) References Cited

U.S. PATENT DOCUMENTS

| 9,067,967 B2 * | 6/2015 | Garcia Anton | C07K 7/06 |
| 2018/0193244 A1 * | 7/2018 | Hood | A61K 8/49 |

FOREIGN PATENT DOCUMENTS

| CN | 106420516 A | 2/2017 |
| CN | 107007516 A | 8/2017 |
| CN | 107898939 A | 4/2018 |
| EP | 2494973 A1 | 9/2012 |
| WO | WO2018101930 A1 | 6/2018 |

OTHER PUBLICATIONS

Database WPI Week 201730 Thomson Scientific, London, GB; An 2017-172106 XP002793235.
Database WPI Week 201762 Thomson Scientific, London, GB; An 2017-546513 XP002793234.
Database WPI Week 201831 Thomson Scientific, London, GB; AN 2018-31464W XP002793236.
Maramaldi Giada et al: Anti-inflammaging and antiglycation activity of a novel botanical ingredient from African biodiversity (Centevita(TM))11 , Clinical. Cosmetic and Investigational Dermatology, Dove Medical Press Ltd, United Kingdom, vol. 7, Jan. 1, 2014 (Jan. 1, 2014), pp. 1-9, XP009514893.

* cited by examiner

*Primary Examiner* — Michael Barker
*Assistant Examiner* — Randall O Winston
(74) *Attorney, Agent, or Firm* — Melissa Krasovec

(57) ABSTRACT

A topical skincare composition including a *Centella asiatica* extract including one or more triterpenes, wherein at least one of the one or more triterpenes is madecassic acid, an *Avena* (oat) extract, a ceramide and a dermatologically acceptable carrier. A method of treating symptoms of itch, redness, flaking, dryness, and/or roughness of the skin, scalp, and/or mucous membrane including the step of applying the topical skincare composition to at least a portion of a user's skin, scalp, and/or mucous membrane in need thereof.

8 Claims, No Drawings

TOPICAL SKINCARE COMPOSITIONS COMPRISING *CENTELLA ASIATICA* SELECTED TRITERPENES

FIELD OF THE INVENTION

The present disclosure relates to topical skincare compositions made from combinations of a *Centella asiatica* extract, an *Avena* (oat) extract, and a ceramide. The present disclosure further relates to methods of treating symptoms of itch, redness, flaking, dryness, and/or roughness of the skin, scalp, and/or mucous membrane using such topical skincare compositions.

BACKGROUND OF THE INVENTION

Challenged skin conditions such as eczema and psoriasis can prove to be frustrating and a nuisance to those who suffer from them. Symptoms of eczema and/or psoriasis may include itch, redness, flaking, dryness, and/or roughness. Itch, redness, flaking, dryness, and/or roughness can occur for a variety of reasons, for instance, in response to an environmental trigger such as cold weather, or an immune trigger such as an allergen response. Such skin conditions may be acute in nature (i.e., occur in a singular, independent incidence) or may be more chronic (i.e., affect the individual for a prolonged period of time). When symptoms of challenged skin occur, the person suffering from the condition generally wishes to alleviate the symptoms as quickly as possible. However, challenged skin may be more sensitive and prone to irritation.

Prescription and over-the-counter steroids can be very effective in relief of symptoms associated with challenged skin. However, it is known that prolonged exposure to steroids may have local and systemic side effects which may include skin atrophy or thinning, telangiectasia, stretch marks, acne, folliculitis, and bruising. Thus instead of using steroids for long-term management, many consumers turn to topical moisturizers.

Topical moisturizers can be an effective adjunct treatment for the long-term management of challenged skin conditions in improving skin health. However, while many moisturizers aim to maintain healthy skin over long-term application, moisturizers are not known to provide fast and/or sufficient relief for those experiencing symptoms of challenged skin. A person experiencing a flare might apply moisturizer and then when the itch, redness, flaking, dryness, and/or roughness is not alleviated quickly enough, the person may stop using the moisturizer in search of a faster-acting treatment, such that the skin does not experience the benefit of the long-term use of a moisturizer. The person might also scratch the affected area while waiting for relief, disrupting the skin further.

Incorporating additional ingredients to speed up relief or to address additional symptoms can be challenging for formulators as the interaction between ingredients on skin biology, especially on challenged skin, is complex and often unpredictable. Topical moisturizers are complex mixtures containing many ingredients and such ingredients can potentially cause undesirable side effects such as increased irritation and/or erythema on the portion of the user's skin to which the topical composition is applied. Users who experience such undesirable side effects might choose to not repurchase the product.

In sum, it is challenging to provide a topical skincare composition that can provide relief of uncomfortable symptoms of challenged skin conditions without resulting in further irritation or other undesirable side effects. Surprisingly, it has been found that a combination of *Centella asiatica* extract having one or more triterpenes, wherein at least one of the one or more triterpenes is madecassic acid, *Avena* (oat) extract, and a ceramide, along with a dermatologically acceptable carrier, can provide for relief of symptoms of challenged skin conditions as well as being acceptable for long-term use and improving skin health without the trade-off of increased irritation and other undesirable side effects.

SUMMARY OF THE INVENTION

The present disclosure relates to topical skincare compositions comprising: a *Centella asiatica* extract comprising one or more triterpenes, wherein at least one of the one or more triterpenes is madecassic acid, an *Avena* (oat) extract, a ceramide, and a dermatologically acceptable carrier.

The present disclosure further relates to methods of treating symptoms of itch, redness, flaking, dryness, and/or irritation of the skin, scalp, and/or mucous membrane. The methods may comprise the steps of: a) providing a topical skincare composition; and b) applying a safe and effective amount of the topical skincare composition to at least a portion of a user's skin, scalp, and/or mucous membrane in need thereof. The topical skincare composition may comprise a *Centella asiatica* extract comprising one or more triterpenes, wherein at least one of the one or more triterpenes is madecassic acid, an *Avena* (oat) extract, a ceramide, and a dermatologically acceptable carrier.

The present disclosure further relates to a topical skincare composition capable of alleviating symptoms associated with eczematous dermatitis, contact dermatitis, atopic dermatitis, seborrheic dermatitis, and/or psoriasis, the topical skincare composition comprising a *Centella asiatica* extract comprising two or more triterpenes, *Avena sativa* (oat) kernel extract, *Avena sativa* (oat) oil, a ceramide, batyl alcohol, caprylyl glycol, 1,2-hexanediol, and a dermatologically acceptable carrier.

DETAILED DESCRIPTION OF THE INVENTION

Definitions

As used herein, the articles "a" and "an" when used in a claim, are understood to mean one or more of what is claimed or described. As used herein, the terms "include," "includes," and "including" are meant to be nonlimiting.

As used herein, the terms "components", "ingredients", and "materials" may be used interchangeably unless otherwise specified.

As used herein "cosmetic agent" means any substance, as well as any component thereof, intended to be rubbed, poured, sprinkled, sprayed, introduced into, or otherwise applied to a mammalian body or any part thereof to provide a cosmetic benefit. Cosmetic agents may include substances that are Generally Recognized as Safe (GRAS) by the United States Food and Drug Administration, food additives, and materials used in non-cosmetic consumer products including over-the-counter medications. A cosmetic agent may include, but is not limited to, (i) chemicals, compounds, small or large molecules, extracts, formulations, or combinations thereof that are known to induce or cause at least one effect (positive or negative) on skin tissue; (ii) chemicals, compounds, small molecules, extracts, formulations, or combinations thereof that are not known have an effect on skin tissue and are discovered, using the provided methods and systems, to induce or cause an effect on skin tissue; and (iii) a compound or combination of compounds that, when applied to skin, provide an acute and/or chronic benefit to skin or a type of cell commonly found therein. Cosmetic agents may regulate and/or improve skin or its associated cells (e.g., improve skin elasticity; improve skin hydration; improve skin condition; and improve cell metabolism).

As used herein, the terms "irritation", "inflammation", "itch", "redness", "burning", "stinging", and "pain" refer to undesirable sensory perceptions, noticeable to a human subject able to report them or measurable by ion channel activation or comparable analytical methodology.

As used herein, the term "topical application" means to apply or spread the compositions of the present disclosure onto the surface of the skin.

The phrase "dermatologically acceptable carrier", as used herein, means that the carrier is suitable for topical application to the keratinous tissue without undue toxicity, incompatibility, instability, allergic response, and the like, has good aesthetic properties, and is compatible with any additional components of the skincare composition.

As used herein, the term "dermatitis" means a condition of the skin in which the skin becomes red, swollen, and/or sore, sometimes with small blisters, resulting from direct irritation of the skin by an external agent or an allergic reaction to it. Examples of dermatitis include, but are not limited to, eczematous dermatitis, contact dermatitis, atopic dermatitis, and/or seborrheic dermatitis.

As used herein, the term "atopic dermatitis" ("AD") is a multifactorial chronic inflammatory skin disorder characterized by genetic barrier defects and allergic inflammation, which is sustained by gene-environmental interactions. AD may be characterized by pruritic and eczematous skin lesions with erythema, excoriation, erosions, lichenification and dryness, frequently accompanied by increased serum immunoglobulin E (IgE) levels. Those with AD may experience areas of severe itching, redness, scaling, and loss of the surface of the skin. AD is a disease arising from the complex interactions between multiple factors, like genetic background, immunologic abnormalities and exposure to environmental sensitizers or allergens. Among these, the dysfunction and breakdown of skin barrier is suggested as an important contributor to the development of AD. The patients with AD generally exhibit xerotic skin resulting from impaired epidermal barrier and the impaired skin barrier function allows the facile penetration of allergens and subsequently stronger sensitization responses, indicating that skin barrier dysfunction plays a critical role in the aggravation and the flares of AD.

As used herein, the term "dermatosis" means a noninflammatory disorder of the skin.

As used herein, the term "keratinous tissue", refers to keratin-containing layers disposed as the outermost protective covering of mammals which includes, but is not limited to, skin, hair, nails, cuticles, etc.

As used herein, the terms "plant extract" or "natural extract" or "extract" with reference to a plant is any material extracted from natural resources including plants. The entire plant or any part of the plant including the bark, berries, flowers, leaves, stem, stalk, peels, resins, rhizome, roots, seeds, woods and mixtures thereof may be used for the extraction process. Extracts may be obtained using any suitable method known in the art including: milling, grinding, maceration, infusion, percolation and decoction, Soxhlet extraction, microwave assisted extraction, ultrasound-assisted extraction, sonication extraction, solvent extraction, accelerated solvent extraction, and supercritical fluid extraction. Suitable extraction solvents may include water, ketones, esters, $C_1$ to $C_6$ alcohols, hydrocarbons and mixtures thereof.

As used herein, the term "safe and effective amount" means an amount of a material, ingredient, compound, component, or composition sufficient to significantly induce a positive benefit, but low enough to avoid serious side effects such as undue toxicity or allergic reaction.

As used herein, the term "skin" means the outermost protective covering of mammals that is composed of cells such as keratinocytes, fibroblasts and melanocytes. Skin includes an outer epidermal layer and an underlying dermal layer. Skin may also include hair follicles, sebaceous gland and nails as well as other types of cells commonly associated with skin, such as, for example, myocytes, Merkel cells, Langerhans cells, macrophages, stem cells, sebocytes, nerve cells and adipocytes.

As used herein, the term "actives", with reference to skincare, means compounds that, when applied to the skin, provide a benefit or improvement to the skin. It is to be understood that skincare actives are useful not only for application to skin, but may also be useful to hair, nails and other mammalian keratinous tissue.

As used herein, the terms "sensitive skin", "hypersensitive skin", and "challenged skin" may include irritable skin and intolerant skin. As used herein, "irritable skin" means skin that reacts through pruritus, i.e., through itching or stinging, to various factors such as the environment, emotions, foods, the wind, rubbing, shaving, hard water with a high calcium or other element concentration, temperature variations, humidity, or wool. As used herein, "intolerant skin" means skin that reacts to various factors, such as the application of cosmetic or dermatological products or soap, through sensations of overheating, tautness, pins and needs, and/or redness.

The terms "substantially free of" or "substantially free from" may be used herein. This means that the indicated material is at the very minimum not deliberately added to the composition to form part of it. The indicated material may be present, if at all, at a level of less than about 0.5%, or less than about 0.01%, or less than about 0.0001%, or less than about 0.000001%, or even 0%, by weight of the composition.

Unless otherwise noted, all component or composition levels are in reference to the active portion of that component or composition, and are exclusive of impurities, for example, residual solvents or by-products, which may be present in commercially available sources of such components or compositions.

All temperatures herein are in degrees Celsius (° C.) unless otherwise indicated. Unless otherwise specified, all measurements herein are conducted at 20° C., under atmospheric pressure, and at 50% relative humidity.

In the present disclosure, all percentages are by weight of the total composition, unless specifically stated otherwise. All ratios are weight ratios, unless specifically stated otherwise.

It should be understood that every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein. Every numerical range given throughout this specification will include every narrower numerical range that falls within such broader numerical range, as if such narrower numerical ranges were all expressly written herein.

Active and other ingredients useful herein may be categorized or described herein by their cosmetic and/or therapeutic benefit or their postulated mode of action. However, it is to be understood that the active and other ingredients useful herein can in some instances provide more than one cosmetic and/or therapeutic benefit or operate via more than one mode of action. Therefore, classifications herein are made for the sake of convenience and are not intended to limit an ingredient to the particularly stated application or applications listed.

Applicant has found that topical skincare compositions of the present disclosure may provide visual and/or therapeutic improvement and/or relief in the skin, scalp, and/or mucous membrane following application of the topical skincare composition and further may be non-irritating to the skin, scalp, and/or mucous membrane.

Without wishing to be bound by theory, Applicant has found that *Centella asiatica* extract may reduce skin irritation caused by an external stimulus by reducing the release of Prostaglandin E2 (PGE2), an inflammatory mediator. Applicant has further found that *Avena* (oat) extract may relieve symptoms of challenged skin by suppressing nuclear factor-kappaB (NFκB) activation, a transcription factor that activates inflammatory response. It is generally known that the incorporation of ceramides in the topical skincare composition may be able to successfully replace depleted ceramides in the skin, thus improving the skin barrier. However, Applicant has surprisingly found that although *Centella asiatica* extract alone may be capable of reducing the potential for irritation, the addition of *Avena* (oat) extract and ceramides to *Centella asiatica* extract greatly reduces the potential for skin irritation in skin care compositions. Applicant has also found that not all *Centella asiatica* extracts are equal in delivering the aforementioned benefits. It is believed that topical skincare compositions of the present disclosure comprising all three ingredients (*Centella asiatica* extract comprising one or more triterpenes wherein at least one of the one or more triterpenes is madecassic acid, *Avena* (oat) extract, and ceramides) result in the relief of symptoms associated with challenged skin symptoms while also having a low potential for skin irritation.

Topical skincare compositions of the present disclosure are soothing compositions not intended to prevent, diagnose, or cure any disease.

I. Topical Skincare Compositions

Topical skincare compositions of the present disclosure may be applied to mammalian keratinous tissue, in particular to human skin. The topical skincare compositions disclosed herein may be useful for providing relief of challenged skin symptoms following application of the composition to the skin. The topical skincare compositions useful in the subject disclosure may be made into a wide variety of product forms such as are known in the art. These may include, but are not limited to, creams, lotions, serums, sprays, tonics, gels, solutions, suspensions, aerosol sprays, sticks, ointments, liquid washes, soap bars, shampoos, hair conditioners, pastes, foams, powders, mousses, shaving creams, hydrogels, film-forming products, and the like. The topical skincare composition form may follow from the particular dermatologically acceptable carrier chosen.

In a non-limiting example, the topical skincare composition may be substantially free of a steroid. While topical and oral steroid therapies are frequently used to provide relief of such symptoms, they do not restore the structure of the lamellar body and lipid bilayer in the lower stratum corneum, which constitute the epidermal barrier function. Preferably, the topical skincare composition may be free of a steroid, or comprise 0%, by weight of the composition, of a steroid. Nonlimiting examples of steroids may include but not limited to, corticosteroids such as hydrocortisone, hydroxyltriamcinolone, alpha-methyl dexamethasone, dexamethasone-phosphate, beclomethasone dipropionates, clobetasol valerate, desonide, desoxymethasone, desoxycorticosterone acetate, dexamethasone, dichlorisone, diflorasone diacetate, diflucortolone valerate, fluadrenolone, fluclorolone acetonide, fludrocortisone, flumethasone pivalate, fluosinolone acetonide, fluocinonide, flucortine butylesters, fluocortolone, fluprednidene (fluprednylidene) acetate, flurandrenolone, halcinonide, hydrocortisone acetate, hydrocortisone butyrate, methylprednisolone, triamcinolone acetonide, cortisone, cortodoxone, flucetonide, fludrocortisone, difluorosone diacetate, fluradrenolone, fludrocortisone, diflurosone diacetate, fluradrenolone acetonide, medrysone, amcinafel, amcinafide, betamethasone and the balance of its esters, chloroprednisone, chlorprednisone acetate, clocortelone, clescinolone, dichlorisone, diflurprednate, flucloronide, flunisolide, fluoromethalone, fluperolone, fluprednisolone, hydrocortisone valerate, hydrocortisone cyclopentylpropionate, hydrocortamate, meprednisone, paramethasone, prednisolone, prednisone, beclomethasone dipropionate, triamcinolone, and mixtures thereof.

*Centella asiatica* Extract

The topical skincare composition may comprise at least 0.000001%, preferably from about 0.00001% to about 5%, more preferably from about 0.0001% to about 1.5%, even more preferably from about 0.001% to about 1.5%, by weight of the composition, of a *Centella asiatica* extract comprising one or more triterpenes, wherein at least one of the one or more triterpenes is madecassic acid. The *Centella asiatica* plant, may also be known as Violette marronne (on Reunion Island), Gotu Kola or Indian pennywort (in India), *Centella repanda* (in North America), Tiger Grass, and Talapetraka (in Madagascar).

Triterpenes are groups of terpenes found in plant gums and resins, having unsaturated molecules based on a unit with the formula $C_{30}H_{48}$. The *Centella asiatica* plant includes the triterpenes of asiatic acid, madecassic acid, asiaticoside, and madecassoside. The biological activity of the *Centella asiatica* plant appears to be due to the presence of triterpene molecules in the plant. In a nonlimiting example, the *Centella asiatica* extract of the present disclosure may comprise two or more triterpenes selected from the group consisting of asiaticoside, asiatic acid, madecassoside, and mixtures thereof. In a nonlimiting example, the *Centella asiatica* extract may comprise from about 20% to about 60%, preferably from about 30% to about 50%, by weight of the *Centella asiatica* extract, of asiaticoside. In a nonlimiting example, the *Centella asiatica* extract may comprise from about 40% to about 80%, preferably from about 50% to about 70%, by weight of the *Centella asiatica* extract, of a mixture of asiatic acid and madecassic acid.

An example of a commercially available *Centella asiatica* extract having one or more triterpenes include the products sold under the tradenames CENTEVITA™ (≥45.0% of the sum of asiaticoside, madecassoside, asiatic acid and madecassic acid; made commercially available by Indena Milan, Italy); *Centella asiatica* Selected Triterpenes (CAST) (having ≥36.0%≤44.0% of asiaticoside, ≥56%≤64.0% of genins as a sum of asiatic acid and madecassic acid; made commercially available by Indena (Milan, Italy); and Titrated Extract of *Centella asiatica* (TECA®) (INCI Name: Asiaticoside (and) Madecassic Acid (and) Asiatic Acid; made commercially available by SEPPIC (Paris, France).

*Avena* (Oat) Extract

The topical skincare composition may comprise at least 0.00001%, preferably from about 0.00001% to about 25%, more preferably from about 0.0001% to about 10%, more preferably from about 0.001% to about 10% by weight of the composition, of an *Avena* (oat) extract.

Preferably, the *Avena* (oat) extract comprises an *Avena sativa* (oat) extract. *Avena sativa*, also referred to as "common oat", is a species of cereal grain most often grown in temperate regions. *Avena sativa* (oat) is made up of the following constituents: amino acids (e.g., lysine, threonine), Avenacins and Avenacosides (i.e., saponins), enzymes (e.g., superoxide dismutase), carbohydrates (e.g., Mucilage (β-glucan), 3%-4% sugar (glucose, fructose), β-glucan, pentosans, saccharose, kestose, neokestose, bifurcose, neobifurcose, and acid galactoarabinoxylan), flavonoids (e.g., kaempferol 3-O-(2",3"-di-E-p-coumaroyl)-α-L-rhamnopyranoside; kaempferol 3-O-(3"-E-p-coumaroyl)-α-L-rhamnopyranoside; kaempferol 3-(2"-O-E-p-coumaroyl)-β-D-glucopyranoside; kaempferol 3-O-β-D-glucopyranoside; kaempferol 7-O-α-L-rhamnopyranoside; linarin; tilianin; myricitrin; quercitrin; kaempferol 3-O-rutinoside; rutin; tricin 7-O-β-D-glucopyranoside; tricin; kaempferol; and luteolin), lipids (e.g., unsaturated triglycerides), phenolic compounds (Avenanthramides, benzoic and cinnamic acids, quinones, flavones, flavonols, chalcones, flavanones, anthocyanidines, and aminophenolics), proteins (e.g., globulin, membrane proteins, soluble proteins of chloroplasts), sterols (e.g., sterols, sterylglycosides, acylated sterylglycosides, and steroidal saponins), and vitamins and minerals (e.g., Vitamin E mostly as α-tocopherol). Constituents of *Avena sativa* (oat) plants may or may not be present in the ingredients, depending on cultivation conditions and extraction process. It is believed that the constituent of Avenanthramides may contribute to the anti-inflammatory and anti-pruritic dermal effects of *Avena* (oat) extract.

The *Avena* (oat) extract may be selected from the group consisting of *Avena* (oat) kernel extract, *Avena* (oat) kernel flour, *Avena* (oat) kernel powder, *Avena* (oat) kernel meal, *Avena* (oat) kernel protein, *Avena* (oat) bran extract, *Avena* (oat) flower/leaf/stem juice, *Avena* (oat) leaf extract, *Avena* (oat) leaf/stalk extract, *Avena* (oat) leaf/stem extract, *Avena* (oat) meal extract, *Avena* (oat) peptide, *Avena* (oat) protein extract, *Avena* (oat) seed extract, *Avena* (oat) seed water, *Avena* (oat) oil, *Avena* (oat) kernel oil, *Avena* (oat) sprout oil, *Avena* (oat) straw extract, hydrolyzed oat flour, hydrolyzed oat protein, hydrolyzed oats, colloidal oatmeal, and mixtures thereof.

In a nonlimiting example, the *Avena* (oat) extract may be selected from the group consisting of *Avena* (oat) kernel extract, *Avena* (oat) oil, colloidal oatmeal, and mixtures thereof. Preferably, the *Avena* (oat) extract may be selected from the group consisting of *Avena sativa* (oat) kernel extract, *Avena sativa* (oat) oil, colloidal oatmeal, and mixtures thereof. Preferably, the *Avena* (oat) oil is *Avena* (oat) kernel oil.

As used herein, "colloidal oatmeal" refers to a finely ground oatmeal and may be from any oat species (i.e., *Avena abyssinica, Avena byzantine, Avena nuda, Avena strigose, Avena, sativa*), and is comprised of at least 94% undamaged oats and may contain, singly or in combination, not more than 25% wild oats.

In a nonlimiting example, the topical skincare composition may comprise from about 0.00001% to about 25%, preferably from about 0.0001% to about 10%, more preferably from about 0.001% to about 5%, more preferably from about 0.1% to about 3%, by weight of the composition, of *Avena* (oat) kernel extract, preferably *Avena sativa* (oat) kernel extract. An example of a commercially available *Avena* (oat) kernel extract is the product sold under the tradename OAT EXTRACT H.GL (INCI name: glycerin (and) aqua (and) *Avena sativa* (oat) kernel extract) made commercially available by the Provital Group. (Barcelona, Spain).

In a nonlimiting example, the topical skincare composition may comprise from about 0.00001% to about 25%, preferably from about 0.0001% to about 10%, more preferably from about 0.001% to about 5%, more preferably from about 0.1% to about 3%, by weight of the composition, of *Avena* (oat) oil, preferably *Avena* (oat) kernel oil, more preferably *Avena sativa* (oat) kernel oil. *Avena* (oat) oil has been noted for its variety and concentration of antioxidants. An example of a commercially available *Avena* (oat) kernel oil extract is the product sold under the tradename AVENALIPID® (INCI Name: *Avena sativa* (oat) kernel oil) made commercially available by Symrise, Inc. (Holzminden, Germany).

In a nonlimiting example, the topical skincare composition may comprise from about 0.00001% to about 25%, preferably from about 0.0001% to about 10%, more preferably from about 0.001% to about 5%, more preferably from about 0.1% to about 3%, by weight of the composition, of *Avena* (oat) kernel extract, preferably *Avena sativa* (oat) kernel extract, and from about 0.00001% to about 25%, preferably from about 0.0001% to about 10%, more preferably from about 0.001% to about 5%, more preferably from about 0.1% to about 3%, by weight of the composition, of *Avena* (oat) oil, preferably *Avena* (oat) kernel oil, more preferably *Avena sativa* (oat) kernel oil.

Ceramides

The topical skincare composition of the present disclosure may comprise at least 0.0001%, preferably from about 0.0001% to about 5%, more preferably from about 0.001% to about 1%, more preferably from about 0.005% to about 0.5%, by weight of the composition, of a ceramide. Ceramides are lipids consisting of a sphingosine linked to a fatty acid or fatty acid derivative via its amine function. It is generally understood that ceramides present within the intercellular lipid lamellae of the stratum corneum have an important structural function in maintaining the water permeability barrier of the skin as ceramide is the main component of the stratum corneum. Ceramides, cholesterol, and saturated fatty acids create a water-impermeable protective organ to prevent excessive water loss due to evaporation as well as a barrier against the entry of pathogens. It is believed that one of the causes of dry, itchy, and/or irritated skin is a reduction in the number of ceramides within these intercellular lipid lamellae. Ceramides may improve long-term moisturization of the skin which in turn, may improve dry, itchy and/or irritated skin. It is therefore desirable to be able to successfully replace these depleted ceramides.

Ceramides suitable for the present disclosure may include ceramide 1, 2, 3, 3B, 4, 5, 6I and 6II. Preferably, the ceramide is selected from the group consisting of ceramide 2, ceramide 3, ceramide 3B, ceramide 4, and mixtures thereof. Preferably, the ceramide is ceramide 3. An example of a commercially available ceramide 3 is the product sold under the tradename Ceramide 3 supplied by Evonik Nutrition & Care GmbH, BL Personal Care (Essen, Germany) (INCI Name: Ceramide NP).

Dermatologically Acceptable Carrier

The topical skincare composition of the present disclosure may comprise a safe and effective amount, for example, from about 50% to about 98%, preferably from about 60% to about 90%, of a dermatologically acceptable carrier ("carrier") for the composition. The carrier can thus act as a diluent, dispersant, solvent, or the like to ensure that the materials can be applied to and distributed evenly over the selected target at an appropriate concentration.

Suitable carriers may include conventional or otherwise known carriers that are dermatologically acceptable. The carrier should also be physically and chemically compatible with the actives as well as any optional materials as described herein, and should not unduly impair stability, efficacy or other use benefits associated with the compositions of the present disclosure. Preferred components of the compositions of this disclosure should be capable of being comingled in a manner such that there is no interaction which would substantially reduce the efficacy of the composition under ordinary use situations.

The dermatologically acceptable carrier may be in a wide variety of forms. Nonlimiting examples may include simple solutions (e.g., aqueous, organic solvent, or oil-based), emulsions, and solid forms (e.g., gels, sticks, flowable solids, wax, amorphous materials). Emulsions may be generally classified as having a continuous aqueous phase (e.g., oil-in water and water-in-oil-in-water) or a continuous oil phase (e.g., water-in-oil and oil-in-water-in-oil). The oil phase of the present disclosure may comprise silicone oils, non-silicone oils such as hydrocarbon oils, esters, ethers, and the like, and mixtures thereof. A suitable dermatologically acceptable carrier is selected to yield a desired product form. Furthermore, the solubility or dispersability of the components may dictate the form and character of the carrier.

The aqueous phase may typically comprise water. However, in other non-limiting examples, the aqueous phase may comprise components other than water, including but not limited to water-soluble moisturizing agents, conditioning agents, anti-microbials, humectants, and/or other water-soluble skin care actives. In a non-limiting example, the non-water component of the composition may comprise a humectant, such as glycerin, and/or other polyols. However, it should be recognized that the composition may be substantially (i.e., less than 1% water) or fully anhydrous.

For emulsions, the topical skincare composition may comprise from at least 0.001%, preferably from about 0.001% to about 15%, more preferably from about 0.1% to about 10%, more preferably from about 0.1% to about 5%, by weight of the topical skincare composition, of an emulsifier/surfactant. The composition may comprise any suitable percentage of emulsifier/surfactant to sufficiently emulsifier the dermatologically acceptable carrier. Suitable surfactants may include but are not limited to non-silicone-containing emulsifiers/surfactants, silicone emulsifiers/surfactants, and mixtures thereof. Emulsifiers/surfactants may be nonionic, anionic, or cationic. Preferred among the nonionic surfactants are those selected from the group consisting of steareth-21, ceteareth-20, ceteareth-12, sucrose cocoate, steareth-100, PEG-100 stearate, cetearyl glucoside, cetearyl alcohol, stearic acid, and mixtures thereof. Suitable emulsifiers are disclosed in, for example, U.S. Pat. Nos. 3,755,560 and 4,421,769. Suitable emulsions may have a wide range of viscosities depending on the desired product form.

The carrier may comprise one or more dermatologically acceptable solid, semi-solid or liquid fillers, diluents, solvents, extenders and the like. The carrier may be solid, semi-solid or liquid in form. The dermatologically acceptable carrier may itself be inert or it may possess dermatological benefits of its own. Concentrations of the carrier may vary with the carrier selected and the intended concentrations of other components of which the topical skincare composition is comprised. As will be understood by one skilled in the art, a given component will distribute primarily into either the aqueous phase or oil phase, depending on the water solubility/dispersability of the component in the composition.

Lipid Bilayer Structurants

The topical skincare composition may comprise at least 0.01%, preferably from about 0.01% to about 20%, more preferably from about 0.1% to about 15%, by weight of the composition, of a lipid bilayer structurant. Lipid bilayer structurants are materials which can favorably interact with and pack the lipid bilayer allowing for improvement of its barrier function and leading to better skin hydration.

The topical skincare composition of the present disclosure may comprise a lipid bilayer structurant selected from the group consisting of batyl alcohol, glyceryl monooleate, isostearyl glyceryl ether, glyceryl isostearate, glyceryl monoerucate, glyceryl oleate, hexadecyl glyceryl ether, glyceryl monostearate, glyceryl monooleate, glyceryl monohydroxystearate, glyceryl monolinoleate, isopropyl isostearate, isopropoyl palmitate, myristyl myristate, myristyl palmitate, myristyl stearate, palmityl palmitate, cetyl stearate, stearyl stearate, isocetyl stearate, isooctadecyl palmitate, isohexadecyl isoctadecanoate, isooctadecanoic acid, 2-hydroxyoctadecyl ester, cetyl glycol isostearate, and mixtures thereof. Preferably, the lipid bilayer structurant is selected from the group consisting of batyl alcohol, isopropyl isostearate, and mixtures thereof.

Preservatives

The topical skincare composition may comprise at least 0.0001%, about 0.001%, about 0.01%, about 0.05%, about 0.1%, about 0.5%, by weight of the composition, a preservative. Preservatives are commonly used in topical skincare compositions to prevent or retard the formation of yeast, bacteria, and/or mold.

The topical skincare composition of the present disclosure may comprise a preservative selected from the group consisting of benzoic acid and salts thereof, benzyl alcohol, benzylhemiformal, benzylparaben, 5-bromo-5-nitro-1,3-dioxane, 2-bromo-2-nitropropane-1,3-diol, butyl paraben, phenoxyethanol, methyl paraben, propyl paraben, diazolidinyl urea, sodium benzoate, calcium benzoate, calcium propionate, caprylyl glycol, biguanide derivatives, captan, chlorhexidine diacetate, chlorhexidine digluconate, chlorhexidine dihydrochloride, chloroacetamide, chlorobutanol, p-chloro-m-cresol, chlorophene, chlorothymol, chloroxylenol, m-cresol, o-cresol, DEDM hydantoin, DEDM hydantoin dilaurate, dehydroacetic acid, diazolidinyl urea, dibromopropamidine diisethionate, DMDM hydantoin, glyceryl caprylate, potassium sorbate, salicylic acid, hexamidine, capryloyl glycine, 1,2-hexanediol, undecylenoyl glycine, ethylhexylglycerin, caprylhydroxamic acid, methylpropanediol, hinokitiol, sodium hinokitiol, phenylethyl alcohol, levulinec acid, p-anisic acid, 2-bromo-2-nitropipane-1,3-diol, sodium hydroxymethylglycinate, iodopropynyl bulylcarbamate, methylchloroisothiazolinone, methylisothiazolinone, piroclone olamine, cinnamon oil, rosemary extract, and combinations thereof.

Emollients

The topical skincare composition may comprise from about 0.001% to about 90%, preferably from about 0.01% to about 50%, more preferably from about 0.1% to about 30%, of the topical skincare composition, of an emollient. Emollients tend to lubricate the skin, increase the smoothness and suppleness of the skin, prevent or relieve dryness of the skin, and/or protect the skin. Emollients may physically prevent or reduce moisture loss from the skin by formation of a water-impenetrable barrier over the stratum corneum. Emollients are typically water-immiscible, oily or waxy materials. The level of emollient within the topical skincare composition, when present, may vary according to the form of the topical skincare composition.

Nonlimiting examples of emollients may include isopropyl isostearate, caprylic/capric triglycerides, petrolatum, dimethicone, dimethiconol, and mixtures thereof. The topical skincare composition may comprise an emollient selected from the group consisting of isopropyl isostearate, caprylic/capric triglycerides, petrolatum, dimethicone, dimethiconol, and mixtures thereof.

Structuring Agent

The topical skincare composition may comprise from about 0.01% to about 15%, preferably from about 0.1% to about 10%, more preferably from about 0.5% to about 5%, by weight of the composition, of a structuring agent. Structuring agents may be particularly preferred in oil-in-water emulsions. Without being limited by theory, it is believed that the structuring agent may assist in providing rheological characteristics to the composition which contribute to the stability of the composition. For example, the structuring agent tends to assist in the formation of the liquid crystalline gel network structures. The structuring agent may also function as an emulsifier or surfactant.

Nonlimiting examples of structuring agents may include stearic acid, palmitic acid, stearyl alcohol, cetyl alcohol, behenyl alcohol, the polyethylene glycol ether of stearyl alcohol having an average of about 1 to about 5 ethylene oxide units, the polyethylene glycol ether of cetyl alcohol having an average of about 1 to about 5 ethylene oxide units, and mixtures thereof. Preferably, the topical skincare composition may comprise a structuring agent selected from the group consisting of stearic acid, palmitic acid, stearyl alcohol, cetyl alcohol, behenyl alcohol, the polyethylene glycol ether of stearyl alcohol having an average of about 2 ethylene oxide units (steareth-2), the polyethylene glycol ether of cetyl alcohol having an average of about 2 ethylene oxide units, and mixtures thereof.

Thickening Agent

Topical skincare compositions may also comprise from about 0.01% to about 10%, preferably from about 0.1% to about 5%, more preferably from about 0.2% to about 5% by weight of the topical skincare composition, of a thickening agent. The thickening agent may be provided in any amount known to one skilled in the art to facilitate achieving the desired viscosity in combination with the other ingredients in the skin care composition. Thickening agents may be used to adjust the viscosity of a composition without substantially changing its other properties. Thickening agents may also improve the suspension of other ingredients. Some thickening agents may also function as stabilizers when they are used to maintain the stability of an emulsion. Thickening agents may be especially useful in products forms such as ointments.

Non-limiting examples of thickeners that may be suitable for use herein include gums, modified gums, starches, modified starches, clays, and cross-linked water swellable polymers. Other non-limiting examples of thickeners are disclosed in U.S. Publication No. 2008/0051497 and U.S. Pat. No. 9,795,552. The topical skincare composition may comprise a thickening agent selected from the group consisting of carboxylic acid polymers, crosslinked polyacrylate polymers, polyacrylamide polymers, polysaccharides, gums, crosslinked vinyl ether/maleic anhydride copolymers, crosslinked poly(N-vinylpyrrolidones), and mixtures thereof. Preferably, the topical skincare composition may comprise a thickening agent selected from the group consisting of carboxylic acid polymers, crosslinked polyacrylate polymers, polyacrylamide polymers, and mixtures thereof, more preferably selected from the group consisting of crosslinked polyacrylate polymers, polyacrylamide polymers, and mixtures thereof.

Humectants

Topical skincare compositions may also comprise from about 1% to about 45%, preferably from about 2.5% to about 25%, more preferably from about 5% to about 15% by weight of the topical skincare composition, of a humectant. Humectants are substances which provide the skin with water-retention benefits. Humectants have an affinity to hydrogen bonds of water molecules and to skin hydrophilic molecular functionalities, and accordingly bind themselves to internal water molecules as well as skin molecules, holding water to the outside surface and upper layers of the stratum corneum, thereby increasing the overall content in the skin itself. Topical application of cosmetic products containing humectants, (for example, glycerin) can be associated with improvements in barrier function, increases in epidermal thickness, and improvements in general skin appearance.

The topical skincare composition may comprise a humectant selected from the group consisting of polyhydric alcohols, amino acids and derivatives thereof such as proline and arginine aspartate, 1,3-butylene glycol, propylene glycol and water and codium tomentosum extract, collagen amino acids or peptides, creatinine, diglycerol, biosaccharide gum-1, glucamine salts, glucuronic acid salts, glutamic acid salts, polyethylene glycol ethers of glycerin (e.g., glycereth 20), glycerin, glycerol monopropoxylate, glycogen, hexylene glycol, honey, and extracts or derivatives thereof, hydrogenated starch hydrolysates, hydrolyzed mucopolysaccharides, inositol, keratin amino acids, glycosaminoglycans, methoxy PEG-10, methyl gluceth-10, methyl gluceth-20, methyl glucose, 3-methyl-1,3-butanediol, N-acetyl glucosamine salts, polyethylene glycol and derivatives thereof (such as PEG-15 butanediol, PEG-4, PEG-5 pentaerythitol, PEG-6, PEG-8, PEG-9), pentaerythitol, 1,2 pentanediol, PPG-1 glyceryl ether, PPG-9,2-pyrrolidone-5-carboxylic acid and its salts such as glyceryl pca, saccharide isomerate, sericin, silk amino acids, sodium acetylhyaluronate, sodium hyaluronate, sodium poly-aspartate, sodium polyglutamate, sorbeth 20, sorbeth 6, sugar and sugar alcohols and derivatives thereof such as glucose, mannose and polyglycerol sorbitol, trehalose, triglycerol, trimethyolpropane, tris (hydroxymethyl) amino methane salts, and yeast extract, and mixtures thereof.

Nonlimiting examples of polyhydric alcohols may include glycerin, diglycerin, glycerol, erythritol, arabitol, xylitol, ribitol, mannitol, sorbitol, galactitol, fucitol, maltitol, mannose, inositol, triethyleneglycol, sodium pyrrolidone carboxylic acid (PCA), zinc PCA and derivatives and mixtures thereof.

Additional Optional Skincare Composition Components

A wide variety of optional skincare composition components may further be included in the topical skincare compositions. For example, the topical skincare composition may comprise a skincare composition component selected from the following absorbents, abrasives, anticaking agents, antifoaming agents, propellants, antimicrobial agents, external analgesics, binders, biological additives, buffering agents, bulking agents, chemical additives, cosmetic biocides, denaturants, cosmetic astringents, drug astringents, film formers, opacifying agents, fragrances, pigments, colorings, essential oils, skin soothing agents, pH adjusters, plasticizers, preservative enhancers, reducing agents, additional skin-conditioning agents, skin penetration enhancing agents, skin protectants, solvents, suspending agents, solubilizing agents, sunscreens, peptides (e.g., peptides containing ten or fewer amino acids, their derivatives, isomers, and complexes with other species such as metal ions), ultraviolet light absorbers or scattering agents, tanning agents, antioxidants and/or radical scavengers, chelating agents, acute powders, oil/sebum control agents, sweat control agents, sequestrants, anti-acne agents, anti-inflammatory agents, anti-androgens, depilation agents, sugar amines (e.g., N-acetyl-glucosamine, desquamation agents/exfoliants, oil control agents, anti-cellulite actives, skin lightening agents, flavonoids, protease inhibitors (e.g., hexamidine and derivatives), non-vitamin antioxidants and radical scavengers, anti-wrinkle actives, anti-atrophy actives, minerals, phytosterols and/or plant hormones, tyrosinase inhibitors, N-acyl amino acid compounds, moisturizers, organic hydroxy acids, vitamins and derivatives thereof, natural or plant extracts, and mixtures thereof. Suitable actives are further described in U.S. Publication Nos. US2006/0275237 A1 to Bissett et al., filed Apr. 21, 2006, and US2004/0175347 A1 to Bissett, filed Mar. 4, 2003. It is noted that one skilled in the art may recognize that an ingredient may have more than one function.

Anti-Inflammatory Agents

The topical skincare composition may comprise a safe and effective amount of an anti-inflammatory agent, preferably from about 0.1% to about 10%, more preferably from about 0.5% to about 5%, by weight of the topical skincare composition. The anti-inflammatory agent may improve the skin appearance benefits of the present disclosure, e.g., such agents contribute to a more uniform and acceptable skin tone or color. The exact amount of anti-inflammatory agent to be used in the compositions will depend on the particular anti-inflammatory agent utilized since such agents vary widely in potency. The anti-inflammatory agent may be selected from the group consisting of non-steroidal anti-inflammatory agents, naturally derived anti-inflammatory agents, and mixtures thereof. Nonlimiting examples of non-steroidal anti-inflammatory agents may include: oxicams (e.g., piroxicam, isoxicam, tenoxicam, and sudoxicam), salicylates (e.g., aspirin, disalcid, benorylate, trilisate, safapryn, solprin, diflunisal, and fendosal); acetic acid derivatives (e.g., diclofenac, fenclofenac, indomethacin, sulindac, tolmetin, isoxepac, furofenac, tiopinac, zidometacin, acematacin, fentiazac, zomepirac, clindanac, oxepinac, felbinac, and ketorolac); fenamates (e.g., mefenamic, meclofenamic, flufenamic, niflumic, and tolfenamic acids), propionic acid derivatives (e.g., ibuprofen, naproxen, benoxaprofen, flurbiprofen, ketoprofen, fenoprofen, fenbufen, indopropfen, pirprofen, carprofen, oxaprozin, pranoprofen, miroprofen, tioxaprofen, suprofen, alminoprofen, and tiaprofenic); and pyrazoles (e.g., phenylbutazone, oxyphenbutazone, feprazone, azapropazone, and trimethazone). Mixtures of these non-steroidal anti-inflammatory agents may also be employed, as well as the dermatologically acceptable salts and esters of these agents.

Naturally derived anti-inflammatory agents may suitably be obtained as an extract by suitable physical and/or chemical isolation from natural sources (e.g., plants, fungi, by-products of microorganisms) or can be synthetically prepared. Nonlimiting examples of naturally derived anti-inflammatory agents may include: candelilla wax, bisabolol (e.g., alpha bisabolol), aloe vera, plant sterols (e.g., phytosterol), Manjistha (extracted from plants in the genus *Rubia*, particularly *Rubia cordifolia*), and Guggal (extracted from plants in the genus *Commiphora*, particularly *Commiphora mukul*), kola extract, chamomile, red clover extract, and sea whip extract, may be used. Additional anti-inflammatory agents useful herein may include compounds of the licorice (the plant genus/species *Glycyrrhiza glabra*) family, including glycyrrhetic acid, glycyrrhizic acid, and derivatives thereof (e.g., salts and esters). Suitable salts of the foregoing compounds may include metal and ammonium salts. Suitable esters may include $C_2$-$C_{24}$ saturated or unsaturated esters of the acids, preferably $C_{10}$-$C_{24}$, more preferably $C_{16}$-$C_{24}$. Nonlimiting examples of the foregoing may include oil soluble licorice extract, the glycyrrhizic and glycyrrhetic acids themselves, monoammonium glycyrrhizinate, monopotassium glycyrrhizinate, dipotassium glycyrrhizinate, 1-beta-glycyrrhetic acid, stearyl glycyrrhetinate, and 3-stearyloxy-glycyrrhetinic acid, and disodium 3-succinyloxy-beta-glycyrrhetinate.

Vitamins and Derivatives Thereof

The topical skincare composition may comprise a safe and effective amount of one or more vitamins and derivatives thereof. Nonlimiting examples of vitamins and derivatives thereof may include B3 compounds such as niacinamide, niacinnicotinic acid, tocopheryl nicotinate; B5 compounds, such as panthenol; vitamin A compounds and natural and/or synthetic analogs of Vitamin A, including retinoids, retinol, retinyl acetate, retinyl palmitate, retinoic acid, retinaldehyde, retinyl propionate, carotenoids (provitamin A); vitamin E compounds, or tocopherol, including tocopheryl sorbate, tocopheryl acetate; vitamin C compounds, including ascorbate, ascorbyl esters of fatty acids, and ascorbic acid derivatives such as magnesium ascorbyl phosphate and sodium ascorbyl phosphate, ascorbyl glucoside, and ascorbyl sorbate), and derivatives of any of the aforementioned actives. The term "derivative" as used herein refers to structures which are not shown but which one skilled in the art would understand are variations of the basic compound.

Skin Soothing Agents

The topical skincare composition may comprise a safe and effective amount of a skin soothing agent, preferably from about 0.1% to about 30%, more preferably from about 0.5% to about 20%, more preferably from about 0.5% to about 10%, by weight of the topical skincare composition. Nonlimiting examples of skin soothing agents suitable for use herein may include panthenoic acid derivatives (including panthenol, dexpanthenol, ethyl panthenol), aloe vera, allantoin, bisabolol, dipotassium glycyrrhizinate, bisabolol, pentylene glycol, 4-t-butylcyclohexanol, PEG-40 hydrogenated castor oil, hydroxyphenyl propamidobenzoic acid, trideceth-9, propylene glycol, *Zingiber officinale* (ginger) root extract, and mixtures thereof. Nonlimiting examples of of suitable commercially available preservatives include SymSitive® (pentylene glycol, 4-t-butylcyclohexanol); SymCare® (pentylene glycol (and) 4-t-butylcyclohexanol (and) PEG-40 hydrogenated castor oil (and) trideceth-9 (and) hydroxyphenyl propamidobenzoic acid (and) propylene glycol); and SymRelief® (bisabolol (and) *Zingiber officinale* (ginger) root extract), all made available by Symrise, Holzminden, Germany).

Acute Powders

The topical skincare composition may comprise a safe and effective amount of an acute powder, preferably from about 0.01% to about 10%, preferably from about 0.05% to about 5%, by weight of the topical skincare composition. Acute powders may modify the optics and/or the feel of the composition product on the skin, such as reducing sticky and/or greasy feel. Acute powders are insoluble powders, generally from about 0.2 to about 40 microns in size. Nonlimiting examples of acute powders may include microthenes, hydrophobic starch particles (e.g., aluminum starch octenylsuccinate, tapioca starch), silicone beads (e.g., polymethylsilsesquioxane), titanium dioxide, beads, and inference pigments. Preferred acute powders may comprise tapioca starch, polymethylsilsesquioxane, or mixtures thereof.

Chelators or Chelating Agents

The topical skincare composition may comprise a safe and effective amount of a chelator or chelating agent, preferably from about 0.1% to about 10%, more preferably from about 1% to about 5%, by weight of the topical skincare composition. As used herein, "chelator" or "chelating agent" means an active agent capable of removing a metal ion from a system by forming a complex so that the metal ion cannot readily participate in or catalyze chemical reactions. The inclusion of a chelating agent is especially useful for providing protection against UV radiation which can contribute to excessive scaling or skin texture changes and against other environmental agents which can cause skin damage.

Propellants

Wherein the topical skincare composition is in the product form of an aerosol, the composition may comprise a propellant. Aerosols are typically applied to the skin as a spray-on product. Aerosols and other spray-on products may be useful in providing broader ranges of coverage of the topical skincare composition in a shorter amount of time than it would take for a user to apply a cream or lotion. Additionally, aerosols and other spray-on products generally allow for the user to apply the topical skincare composition without having to utilize the fingers and/or any useful spreading tools (such as, for example, towels, wipes, tissues, and the like) to spread the topical skincare composition onto the skin, minimizing risk of contaminating the affected situs with any additional bacteria from the fingers and/or spreading tools and minimizing clean-up for the user of the fingers and/or spreading tools.

Viscosity and pH of the Topical Skincare Composition

The viscosity and pH of the topical skincare composition of the present disclosure may depend on the type or form of product form desired for the composition. Generally, the topical skincare composition may have a viscosity of from about 30,000 cP to about 300,000 cP when measured according to the Viscosity Test Method described herein. The viscosity of the composition as used herein is described as the Brookfield viscosity.

Nonlimiting exemplary topical skincare compositions of the present disclosure wherein the composition is in the form of a lotion may have a viscosity of from about 30,000 cP to about 100,000 cP. Nonlimiting exemplary topical skincare compositions of the present disclosure wherein the composition is in the form of a cream may have a viscosity of from about 50,000 cP to about 300,000 cP. Nonlimiting exemplary topical skincare compositions of the present disclosure wherein the composition is in the form of a serum may have a viscosity of from about 10,000 cP to about 30,000 cP. Viscosity is measured according to the Viscosity Test Method as described herein.

The topical skincare compositions of the present disclosure are preferably formulated to have a pH of 10.5 or below. The pH values of these compositions preferably range from about 2 to about 10.5, more preferably from about 3 to about 8, even more preferably from about 4 to about 7. pH is measured according to the pH Test Method as described herein.

Methods of Making Topical Skincare Compositions

The topical skincare compositions of the present disclosure may be generally prepared by conventional methods such as are known in the art of making topical compositions. Such methods typically involve mixing of the ingredients in one or more steps to a relatively uniform state, with or without heating, cooling, application of vacuum, and the like. Typically, emulsions may be prepared by first mixing the aqueous phase materials separately from the fatty phase materials and then combining the two phases as appropriate to yield the desired continuous phase. The compositions may preferably be prepared such as to optimize stability (e.g., physical stability, chemical stability) and/or delivery of the active materials.

Methods of Using Topical Skincare Compositions

Topical skincare compositions of the present disclosure may be used to treat symptoms of itch, redness, flaking, dryness, and/or roughness of the skin, scalp, and/or mucous membrane. The treatment method may include the steps of providing a topical skincare composition according to the present disclosure and applying a safe and effective amount of the topical skincare composition to at least a portion of a user's skin, scalp, and/or mucous membrane in need thereof.

The itch, redness, flaking, dryness, and/or roughness may be associated with at least one skin, scalp, and/or mucous membrane condition selected from the group consisting of eczematous dermatitis, contact dermatitis, atopic dermatitis, and psoriasis. Other conditions wherein itching, redness, flaking, dryness, and/or roughness may be experienced are also contemplated. The topical skincare composition may also be applied to the skin in need thereof, including but not limited to the affected situs, the surrounding skin, and generally the skin all over the body, when there are active flares present as well as when there are no active flares present. The portion of the user's skin, scalp, and/or mucous membrane in need thereof may be presently affected by one or more of the following: rash, scaling, lesions, fissures, and/or bumps, or, none of the above may be present. The term "skin, scalp, and/or mucous membrane in need thereof", is meant to be construed as narrowly as the affected situs where itch, redness, flaking, dryness, and/or roughness is present and/or where an active flare is present to as broadly as the skin of the body as a whole. The topical skincare composition may provide the benefit of relief, preferably fast relief, of itch, redness, flaking, dryness, and/or roughness as well as other bothersome symptoms associated with eczematous dermatitis, contact dermatitis, atopic dermatitis, and/or psoriasis during active flares. By "relief", it is meant that the user may feel relief or improvement of the symptoms after applying the topical skincare composition. By "fast relief", it is meant that the user may feel relief or improvement of the symptoms immediately after applying the topical skincare composition, within one about (1) day after applying the topical skincare composition, within about four (4) days after applying the topical skincare composition, within about one (1) week after applying the topical skincare composition, within about two (2) weeks after applying the topical skincare composition, within about four (4) weeks after applying the topical skincare composition, within about eight (8) weeks after applying the topical skincare composition, and so on, generally less than about twelve (12) weeks after applying the topical skincare composition. Preferably, the topical skincare composition may provide the benefit of fast relief of itch, redness, flaking, dryness, and/or roughness as well as other bothersome symptoms associated with eczematous dermatitis, contact dermatitis, atopic dermatitis, and/or psoriasis during active flares within one (1) to seven (7) days after applying the topical skincare application.

The method may include the step of providing a topical skincare composition according to the present disclosure. The topical skincare composition may be in any product form that enables a user to apply the composition to the user's skin, scalp, and/or mucous membrane. Examples include, but are not limited to, the product forms as disclosed herein. The topical skincare composition may be provided in a vessel depending upon the product form, such as for example, in a jar, in a squeeze tube, in a bottle, in a canister, or any such vessel known to one skilled in the art to deliver topical skincare compositions.

Many regimens exist for the application of topical skincare compositions. The step of applying a safe and effective amount of the topical skincare composition to at least a portion of a user's skin, scalp, and/or mucous membrane in need thereof may be performed, by way of nonlimiting example, as follows. A user may obtain the provided topical skincare composition and apply a liberal amount of the topical skincare composition to the skin, scalp, and/or mucous membrane in need thereof, preferably with even more liberal application any affected situses and area surrounding the affected situses. The step of applying the topical skincare composition to the portion of the user's skin, scalp, and/or mucous membrane in need thereof may comprise applying from about 0.01 g/m$^2$ to about 20 g/m$^2$, or from about 0.05 g/m$^2$ to 15 g/m$^2$, or from about 0.1 g/m$^2$ to about 10 g/m$^2$ of the topical skincare composition.

In a nonlimiting example, the step of applying the topical skincare composition to the portion of the user's skin, scalp, and/or mucous membrane in need thereof is repeated at least once, preferably at least twice, or on a more frequent basis, within a twenty-four-hour time period. In a nonlimiting example, the step of applying the topical skincare composition to the portion of the user's skin, scalp, and/or mucous membrane in need thereof is repeated at least once, preferably at least twice, within a twenty-four-hour time period. When applied twice daily, the first and second applications may be separated by at least 1 to 12 hours. Typically, the topical skincare composition may be applied in the morning and/or in the evening before bed.

The step of applying the topical skincare composition may be repeated during a treatment period. The treatment period is ideally of sufficient time to provide a relief or improvement of itch, redness, flaking, dryness, and/or roughness and to also improve skin health. The treatment period may be up until the user experiences relief or improvement in itch, redness, flaking, dryness, and/or roughness, but preferably the treatment period continues even after the user experiences relief or improvement in itch, redness, flaking, dryness, and/or roughness so that the topical skincare composition may gradually improve the health of the skin. Long-term application of the topical skincare composition after the user experiences relief or improvement of challenged skin symptoms may potentially lessen the frequency and/or severity of future occurrences of challenged skin symptoms. The treatment period may be at least 2 consecutive days, at least 3 consecutive days, at least 4 consecutive days, at least 5 consecutive days, at least 6 consecutive days, at least 1 week, at least 2 weeks, at least 3 weeks, at least 4 weeks, at least 5 weeks, at least 6 weeks, at least 7 weeks, at least 8 weeks, and so on. The treatment period may extend over multiple months (i.e., 3-12 months) or multiple years. In a nonlimiting example, the topical skincare composition may be applied at least once, preferably at least twice, a day during a treatment period of at least 1 week, about 2 weeks, about 3 weeks, or about 4 weeks. The topical skincare composition may be concurrently applied in addition to any other prescription and/or non-prescription compositions the user may be taking.

In a nonlimiting example, after application of the topical skincare composition to the user's skin, scalp, and/or mucous membrane in need thereof, the topical skincare composition is not removed for at least five minutes. Applicant has found that even leaving the topical skincare composition without removal for at least five minutes may provide some relief or improvement of itch, redness, flaking, dryness, and/or roughness of the skin, scalp, and/or mucous membrane. Preferably, the topical skincare composition is not removed for at least thirty minutes, more preferably for at least one hour, even more preferably for at least several hours, or until the next application of the topical skincare composition. In applications such as when the topical skincare composition is used for the scalp as a rinse-off product, it is particularly beneficial for the topical skincare composition to not be removed for at least five minutes. A user may cleanse the skin, scalp, and/or mucous membrane prior to application of the topical skincare composition such as by using a bar of soap or other conventional cleansers. A user may apply the topical skincare composition without cleansing the skin, scalp, and/or mucous membrane prior to application. After applying the topical skincare composition, a user may occlude the topical skincare composition with, for example, a bandage. Occluding with a bandage may keep the topical skincare composition from being rubbed off of the skin, scalp, and/or mucous membrane by external objects, allowing for longer exposure of the skin, scalp, and/or mucous membrane to the composition.

Test Methods

Viscosity Test Method

The viscosity of samples can be measured using a standard viscometer, such as, for example, a Brookfield DV2T viscometer (manufactured by Brookfield Ametek, Middleboro, Mass., U.S.A.), fitted with a helipath T-bar spindle type T-C. The viscometer is leveled, setup and calibrated according to the manufacturer's standards. The viscometer speed (RPM) is selected to ensure the measured viscosity is within the manufacturer's recommended settings (e.g., 5 RPM).

Samples are stored in sealed glass jars with an opening and internal diameter of at least 40 mm and filled to a height of at least 50 mm with care taken to avoid entrapped air bubbles. Centrifugation may be used to help removed entrained air. Sample jars are equilibrated at 23° C.±2° C. and about 50%±2% relative humidity for at least 24 hours prior to measurement.

Viscosity is measured at 23° C.±2° C. and about 50%±2% relative humidity by placing the uncapped sample jar under the viscometer and lowering the viscometer until the tip of the T-bar touches the surface of the sample. The descending helipath is turned on and a timer started once the cross-bar of the T-bar touches the surface of the sample. A reading is taken about every 10 seconds over the time period of between about 45 seconds and about 1 minute. The viscosity is calculated as the arithmetic average of the viscosities recorded. Care is taken to ensure the T-bar does not touch the glass jar.

pH Test Method pH can be using a standard pH meter such as, for example, a Beckman Coulter model PHI1410 pH meter equipped with a general-purpose probe (manufactured by Beckman Coulter, Brea, Calif., U.S.A.). The pH meter is calibrated according to the manufacturer's instructions. Measurements are performed after storing the compositions at room temperature (approximately 23° C.±2° C.) for approximately 24 hours.

Signature Free Method of Querying Perturbagens Using Connectivity Mapping to Test Similarity Among Different Varieties of Perturbagens The signature-free query method describes methodologies for identifying gene expression similarities among different perturbagens, such as cosmetic actives and/or natural extracts in an already existing tert connectivity map database. "Connectivity map" and "C-map" refer broadly to devices, systems, articles of manufacture, and methodologies for identifying relationships between cellular phenotypes or cosmetic conditions, gene expression, and perturbagens, such as cosmetic actives. A description of connectivity mapping and methods of using connectivity mapping to identify genes and/or compositions of interest can be found in U.S. Publication No. 2012/0283112 titled filed by Binder, et al., on Feb. 22, 2012 and U.S. Publication Nos. 2013/0259816, 2013/0261006, 2013/0261024 and 2013/0261007 all filed by Hakozaki, et al., on Mar. 27, 2013.

"Connectivity score" refers to a derived value representing the degree to which an instance correlates to a query. "Query" refers to data that is used as an input to a connectivity map and against which a plurality of instances are compared. A query may include a gene expression signature associated with one or both of a skin aging condition and a benchmark skin agent. "Instance" refers to data from a gene expression profiling experiment in which skin cells are dosed with a perturbagen. In some examples, the data may comprise a list of identifiers representing the genes that are part of the gene expression profiling experiment. The identifiers may include gene names, gene symbols, microarray probe set IDs, or any other identifier. In some examples, an instance may comprise data from a microarray experiment and comprises a list of probe set IDs of the microarray ordered by their extent of differential expression relative to a control. The data may also comprise metadata, including but not limited to data relating to one or more of the perturbagen, the gene expression profiling test conditions, the skin cells, and the microarray.

The tert C-map database consists of normalized gene expression data of approximately 3200 perturbagens. The data is normalized by applying one of a variety of normalization techniques generally known by one skilled in the art. By way of example, and without limitation, the normalization technique employed may be a MASS algorithm for generating gene expression summaries or a robust multi-array average (RMA) algorithm. For each individual perturbagen, the output of the normalization includes an expression value for each probe analyzed in the gene expression profiling experiment.

A subset of gene probes is selected accordingly. In some examples, the subset of probes may include the 5,000-10,000 probes with the highest average expression values. The subset of probes may be selected according to the probes that have average expression values higher than a predetermined threshold. In some nonlimiting examples, the expression values may be log transformed before any further processing takes place. In other nonlimiting examples, further processing is performed on the raw normalized expression values. In the C-map database, all of the gene expression data from all of the perturbagens is combined into a single data matrix.

The data matrix is analyzed using multivariate statistical analysis. Though described herein with reference to regularized Fisher Discriminant Analysis using a kernel version of the projection matrix, those of ordinary skill in the art will readily appreciate that other forms of multivariate statistical analysis may be employed in other embodiments. By way of nonlimiting example, a non-kernel version of a projection matrix, a non-regularized Fisher Discriminant Analysis, a Linear Discriminant Analysis, or Generalized Linear Discriminant Analysis could be employed. In any event, the data matrix is reduced by removing non-replicated instances (e.g., instances for perturbagens having only a single genetic expression profile). A projection matrix (or function) is learned using the multivariate statistical analysis, and the entire data matrix (i.e., not the reduced matrix), is projected onto the projection space using the projection matrix (or function). (When using a Kernel version of Fisher Discriminant Analysis, the result is a projection function that utilizes the kernel function to compute the projection. The resulting matrix has a significantly reduced dimension. Similarly to principal component analysis, less significant dimensions can be further dropped to improve the performance of the resulting matrix. The parameters for the regularized Fisher Discriminant Analysis and the number of dimensions to keep for the final projected matrix are determined by cross-validation.

A perturbagen is selected, and the distance in the projected space between the selected perturbagen and every other perturbagen can be calculated using either cosine distance or Euclidean distance. Each of the perturbagens in the C-map database can be ranked according to its distance from the selected perturbagen. The resulting matrix is then used to compute a similarity (distance matrix) among all the perturbagens tested.

PGE2 Assay

Redness and swelling upon application of a material or combination of materials in skin is associated with an increase in generation of inflammatory mediators such as the Prostaglandin E2 ("PGE2") mediator. Measuring the amount of PGE2 generation in keratinocytes in-vitro upon application of a material may provide an estimate of whether a material or a combination of materials is likely to result in skin irritancy when applied on skin, as described in further detail in PCT application WO 93/17336.

The following assay may be used to estimate the generation of PGE2 in-vitro. Tert-keratinocytes are cultured until they reach a confluency of ~80%. Dilutions of indicated treatments are added to understand the effect of each material on PGE2 generation. Arachidonic acid (~2.5 µg/mL) is also included in the treatment media for all samples as a substrate to form PGE2. The treated cells are then cultured overnight with supernatants harvested for PGE2 quantitation using a homogeneous time resolved fluorescence (HTRF®) technology system (made commercially available by Cis-Bio, Bedford, Mass., U.S.A.). The cells are then assayed for ATP using the CELLTITER-GLO® Assay system (made commercially available by Promega, Madison, Wis., U.S.A.). PGE2 release is normalized to ATP. The amount of PGE2 measured upon addition of materials is compared to the baseline in which no chemical was added (culture media only).

NF-κB Test Method

The NF-κB Test Method as described herein may identify materials that suppress NF-κB. Nuclear factor-kappaB ("NF-κB") is associated with inflammation, immune response, cell proliferation and protection against apoptosis. NF-κB is a first responder to harmful cellular stimuli. NF-κB is a transcription factor that activates the expression of multiple genes that are involved in the inflammatory and immune response. Compounds that suppress NF-κB activation are known to have anti-inflammatory benefits.

10,000 HEK293 cells are cultured in high glucose DMEM media and are grown for approximately 72 hours. Once cells have grown, dilutions of indicated treatments are added to cells in media and incubated for approximately 30-60 minutes. After the prescribed time has elapsed, cells are stimulated with tumor necrosis factor alpha ("TNFα") for approximately 3-4 hours. After the prescribed time has elapsed, cells are ready to be treated and analyzed according the manufacturer's instructions for LiveBLAzer™-FRET B/G loading kit (commercially available from Thermo Fisher Scientific, Waltham, Mass., U.S.A.) Cells are then incubated for two hours Once the two hours have passed, plates are read under LiveBLAzer™-reporter assay protocol using SYNERGY™ NEO Gen5™ Data Analysis Software (commercially available from BioTek, Winooski, Vt., U.S.A.). A general dual mirror is used. Filters for protocol: excitation filter is Photometric 405; emission filter is FITC 535; second emission filter is Umbelliferone 460. The emission ratios (Em 460/Em 535) are saved in a single .txt file and imported into Assay Explorer for data analysis and storage.

The following controls are run on each plate:
High control (Stimulated)=cells+TNFα+1% DMSO
Blank (Unstimulated)=cells+DMSO
Standard (Positive control inhibitor)=cells+TNFα+Fisetin
Negative Control (no cells)=assay medium
Final assay concentrations are calculated.

To measure the anti-inflammatory benefits of the individual ingredients, each ingredient is tested at four different concentrations (0.5%, 0.125%, 0.03125%, and 0.0078125%) and the Percent Inhibition Calculation ("IC50") is calculated. The IC50 is a measurement used to determine the concentration that is needed for a compound to elicit 50% inhibition of NF-κB activation. An ingredient is described as non-inhibitory ("NI") when it does not inhibit NF-κB activity in any of the specified concentrations.

The IC50 is calculated according to the following equation:

$$IC50 = \frac{\text{High Control} - \text{Sample}}{\text{High Control} - \text{Blank}} \times 100$$

Sample=460/535 ratio of well containing cells+TNFα+compound (n=1)
High Control=Average 460/535 ratio of wells containing cells+TNFα+DMSO (n=4)
Blank=Average 460/535 ratio of wells containing cells+DMSO (n=4)

EXAMPLES

The following data and examples, including comparative examples, are provided to help illustrate the topical skincare compositions described herein. The exemplified compositions are given solely for the purpose of illustration and are not to be construed as limitations of the present disclosure, as many variations thereof are possible without departing from the spirit and scope of the disclosure. All parts, percentages, and ratios herein are by weight unless otherwise specified.

A summary of the following data is provided: Examples 1 and 2 tested ingredients of topical skincare compositions according to the present disclosure in two separate bioassays known to be associated with inflammatory response. The PGE2 data of Example 1 and the NF-κB data of Example 2 suggest that *Avena* (oat) extract and *Centella asiatica* extract mitigate different inflammatory cascades and therefore may be effective when incorporated in topical skincare compositions. Particularly, the PGE2 data of Example 1 suggests that *Centella asiatica* extract alone reduces the release of PGE2, an inflammatory mediator involved with the sensation of irritation of the skin when coming into contact with an outside stimulus. Based on the bioassay results from Examples 1 and 2, a series of compositions were prepared varying the combination of actives (*Centella asiatica* extract, *Avena* (oat) extract, and ceramide) (Example 3) and a series of consumer tests were conducted (Example 4) to understand the consumer acceptance of each formula in both relief of symptoms and being non-irritating to the skin. The consumer data generated in Example 4 demonstrates that compositions having only *Centella asiatica* extract may provide good relief of symptoms (Examples 4A and 4B), however, *Centella asiatica* extract alone may be insufficient, as surprisingly there are still instances of irritation (Example 4C). Lastly, Example 5 demonstrates that the not all varieties of *Centella asiatica* extract have the same functional activity and thus selecting a particular *Centella asiatica* extract to provide the aforementioned benefits of the present disclosure is needed. In sum, Applicant has demonstrated that the particular combination of ingredients according to the present disclosure provides topical skincare compositions that provide relief of symptoms and are non-irritating to the skin.

Example 1: PGE2 Assay of Ingredients of Topical Skincare Compositions

Analysis of the effects of different ingredients on skin irritancy using the inflammatory mediator Prostaglandin E2 (PGE2) was run according to the PGE2 Assay as described herein. Standard deviation and p-value versus *Centella asiatica* Selected Triterpenes (CAST) were then calculated. The results of the PGE2 Assay for the different ingredients is summarized in Table 1 below.

TABLE 1

Summary of PGE2 Assay Data

| Example | Centella Asiatica Selected Triterpenes[1] 0.0001% | Avena sativa (Oat) Extract[2] 0.0001% | Ceramide[3] 0.0001% | Average PGE2 | Standard Deviation | P-Value vs. CAST |
|---|---|---|---|---|---|---|
| 1A |   | + | + | 78.25 | 9.00 | 0.00 |
| 1B | + |   |   | 52 | 7.44 | 1.00 |
| 1C | + | + | + | 49 | 8.29 | 0.61 |

[1]*Centella Asiatica* Selected Triterpenes (CAST), having ≥36.0% ≤ 44.0% of asiaticoside, ≥56% ≤ 64.0% of genins as a sum of asiatic acid and madecassic acid) made commercially available by Indena (Milan, Italy).
[2]Oat Extract H.GL. - M.S. 46080 supplied by the Provital Group (Barcelona, Spain).
[3]Ceramide 3 supplied by Evonik Nutrition & Care GmbH, BL Personal Care (Essen, Germany).

As shown in Table 1, Example 1A, (*Avena sativa* (oat) extract and ceramide), showed a less than 25% reduction in release of PGE2 release in comparison with Examples 1B and 1C (both having *Centella asiatica* extract), which showed a greater than 40% reduction in release of PGE2. The results demonstrate that the presence of *Centella asiatica* Selected Triterpenes reduces the release of PGE2, an inflammatory mediator.

Example 2: NF-κB Test Method to Measure the Anti-Inflammatory Benefits of Ingredients of Topical Skincare Compositions Measurement of the anti-inflammatory benefits of different ingredients of topical skincare compositions according to the present disclosure was tested according to the NF-κB Test Method as described herein. Each ingredient was tested at four different concentrations (0.5%, 0.125%, 0.03125%, and 0.0078125%). The results of the NF-κB Test Method and percent inhibition calculation (IC50) for the different ingredients is summarized in Table 2 below.

TABLE 2

Summary of NF-κB Test Method and percent inhibition calculation (IC50)

| Ingredient | NF-κB IC50 |
|---|---|
| *Centella Asiatica* Selected Triterpenes[1] | 2% |
| Avena (oat) oil extract[2] | 0.08% |
| Avena (oat) kernel extract[3] | 0.08% |
| Ceramide[4] | NI |

[1]*Centella Asiatica* Selected Triterpenes (CAST), having ≥36.0% ≤ 44.0% of asiaticoside, ≥56% ≤ 64.0% of genins as a sum of asiatic acid and madecassic acid) made commercially available by Indena (Milan, Italy).
[2]AVENALIPID ® supplied by Symrise, Inc. (Holzminden, Germany).
[3]Oat Extract H.GL. - M.S. 46080 supplied by the Provital Group (Barcelona, Spain).
[4]Ceramide 3 supplied by Evonik Nutrition & Care GmbH, BL Personal Care (Essen, Germany).

As shown in Table 2, of the four ingredients evaluated, the Avena (oat) oil extract and the Avena (oat) kernel extract each had an IC50 at a concentration of 0.08%, suggesting a strong NF-κB inhibitory activity, whereas *Centella asiatica* Selected Triterpenes (CAST), had an IC50 of 2%, suggesting less potency. Ceramide had no NF-κB activity. As such, Example 2 demonstrates that Avena (oat) extracts have superior potency to mitigate NF-κB associated inflammation.

Example 3: Examples of Topical Skincare Compositions

A series of compositions were prepared varying the combination of actives (*Centella asiatica* extract, Avena (oat) extract, and ceramide) to understand the consumer acceptance of each formula. Test Composition 1 and Comparative Compositions 1-3, shown below in Tables 3 and 4, were prepared according to the procedure described hereinafter.

Phase A was prepared by adding all of the Phase A ingredients to a beaker, heating the ingredients to between about 70° C. and about 80° C., and mixing with an overhead mixer. Phase B was prepared by combining all of the Phase B ingredients in a separate beaker equipped with a stir bar and heating the ingredients to between about 70° C. and about 80° C. Phase D was prepared by combining all of the Phase D ingredients in a separate beaker equipped with a stir bar and heating the ingredients to between about 45° C. and about 55° C.

The following took place under continuous mixing using an overhead mixer. Phase B was poured into Phase A and the resulting mixture was milled. The mixture was then cooled to between about 55° C. and about 65° C. The individual ingredient of Phase C was then added directly to the mixture and the resulting mixture was milled again. The mixture was then cooled to between about 45° C. and about 55° C. For compositions containing *Centella asiatica* extract, the ingredients of Phase D were then added to the mixture. For compositions containing *Centella asiatica* extract, the ingredient of Phase E was added to the beaker previously used for Phase D, and then added to the mixture. The ingredients of Phase F were then individually added to the mixture and the resulting mixture was milled. The mixture was cooled to between about 35° C. and about 45° C. The composition was then poured into a suitable container, labeled, and stored for future pH and viscosity measurements. Suitable instruments may include, for example, beakers equipped with an IKA digital overhead mixer equipped with a propeller blade, IKA RET control visc magnetic stir plates with heating probes, IKA T25 Ultra Turrax homogenizers (all manufactured by IKA, Wilmington, N.C.).

TABLE 3

Topical Skincare Compositions, mass %

| Phase | Ingredient | Test Composition 1 | Comparative Composition 1 | Comparative Composition 2 | Comparative Composition 3 |
|---|---|---|---|---|---|
| A | Carrier[1] | Balance | Balance | Balance | Balance |
| A | Humectant[2] | 10.000 | 10.000 | 10.000 | 10.000 |
| A | Skin soothing agent[3] | 1.000 | 1.000 | 1.000 | 1.000 |
| A | Chelant[4] | 0.100 | 0.100 | 0.100 | 0.100 |
| A | pH adjustor[5] | 0.022 | 0.022 | 0.022 | 0.022 |
| B | Emollient[6] | 4.100 | 4.100 | 4.100 | 4.100 |
| B | Vitamins and derivatives thereof[7] | 0.600 | 0.600 | 0.600 | 0.600 |
| B | Emulsifier/surfactant[8] | 0.400 | 0.200 | 0.200 | 0.200 |
| B | Structuring Agent[9] | 1.580 | 1.580 | 1.580 | 1.580 |
| B | Avena (oat) oil extract[10] | 1.000 | 0.000 | 1.000 | 0.000 |
| B | Ceramide[11] | 0.050 | 0.000 | 0.050 | 0.000 |
| C | Thickening agent[12] | 2.300 | 2.300 | 2.300 | 2.300 |
| D | *Centella Asiatica* extract[13] | 0.006 | 0.000 | 0.000 | 0.006 |

TABLE 3-continued

| | | Topical Skincare Compositions, mass % | | | |
|---|---|---|---|---|---|
| Phase | Ingredient | Test Composition 1 | Comparative Composition 1 | Comparative Composition 2 | Comparative Composition 3 |
| D | Preservative[14] | 0.375 | 0.000 | 0.000 | 0.375 |
| E | Carrier[1] | 0.050 | 0.000 | 0.000 | 0.050 |
| F | Preservative[14] | 0.000 | 0.375 | 0.375 | 0.000 |
| F | Emollient[15] | 1.000-1.140 | 1.140 | 1.000 | 1.14 |
| F | Avena (oat) kernel extract[16] | 0.500 | 0.000 | 0.500 | 0.000 |
| F | Acute Powder[17] | 2.000 | 2.000 | 2.000 | 2.000 |
| | Total | 100 | 100 | 100 | 100 |

Raw Materials for Table 3
[1]United States Pharmacopeia (USP) Purified Water Wash.
[2]Glycerin EP
[3]Dexpanthenol
[4]Disodium EDTA
[5]Sodium hydroxide
[6]Isopropyl isostearate, caprylic/capric triglycerides, petrolatum.
[7]DL-alpha Tocopheryl acetate (Vitamin E)
[8]Cetearyl glucoside and cetearyl alcohol, polyethylene glycol (PEG) 100 stearate, stearic acid.
[9]Stearyl alcohol, cetyl alcohol 95%, behenyl alcohol 75%
[10]AVENALIPID ® supplied by Symrise, Inc. (Holzminden, Germany).
[11]Ceramide 3 supplied by Evonik Nutrition & Care GmbH, BL Personal Care (Essen, Germany).
[12]Caprylic/capric triglycerides and sodium acrylates copolymer.
[13]*Centella Asiatica* Selected Triterpenes (CAST) supplied by Indena (Milan, Italy). HPLC content: ≥36.0% ≤ 44.0% of asiaticoside, ≥56% ≤ 64% of genins as a sum of asiatic acid and madecassic acid. Form: white powder. Solubility: soluble in propylene glycol, ethoxydiglycol, polyethyleneglycol 600, polyoxyethylene sorbitan monooleate.
[14]Phenoxyethanol NF.
[15]Dimethicone and dimethiconol.
[16]Oat Extract H.GL. - M.S. 46080 supplied by the Provital Group (Barcelona, Spain).
[17]Tapioca starch (and) polymethylsilsesquioxane starch is a non-GMO, aluminum free, modified tapioca starch commercially available under the tradename DRY-FLO ® TS as sold by AkzoNobel (Amsterdam, Netherlands).

Each of Test Composition 1 and Comparative Compositions 1-3 shown above contains a different combination of *Centella asiatica* extract, *Avena* (oat) extract, and ceramides.

Table 4 below shows the viscosity and pH for each of Test Composition 1 and Comparative Compositions 1-3. Viscosity was measured according to the Viscosity Test Method described herein. pH was measured according to the pH Test Method described herein.

TABLE 4

| | Topical Skincare Composition Aesthetics | | | |
|---|---|---|---|---|
| | Test Composition 1 | Comparative Composition 1 | Comparative Composition 2 | Comparative Composition 3 |
| Viscosity (cP) | 95,600 | 88,000 | 84,600 | 102,000 |
| pH | 5.84 | 6.02 | 5.93 | 5.99 |

Example 4: Consumer Study on Topical Skincare Compositions According to the Present Disclosure vs. Comparative Compositions Applicant conducted a blind and instructed, daily, single product use test over a 7-day period. Two separate tests were run, Test 1 and Test 2. Participants were male and female between eighteen (18) and sixty-five (65) years of age who met all three of the following criteria at the beginning of the test period: 1) participants had eczema (self-reported); 2) participants had an active flare (self-reported wherein the active flare was not only on the scalp); and 3) participants had a self-reported itch rating of 5 or higher on a 0-10 scale (0=no itch, 10=severe itch when asked to rate on average how itchy participant's eczema (Test 1) or skin (Test 2) lesions have been when thinking about participant's skin over the last 3 days or nights). In Test 2, participants also were required to have dry, itchy skin. Pregnant or nursing women and those allergic to oats were excluded from participating in the test.

Each participant was provided with a test product in a tube labeled "eczema cream" (Test 1) or "cream for dry, itchy eczema-prone skin" (Test 2), containing the Test Composition 1 or one of Comparative Compositions 1, 2, or 3, as prepared according to Example 3. Participants were instructed to apply the test product twice a day each day of the test period. Participants were further instructed not to use any over-the-counter cleansers, lotions, creams, and/or body oils during the test period. Participants were instructed that they should continue any products prescribed by a physician during the duration of the test period.

Participants completed a questionnaire immediately preceding the start of the test period, and immediately after completing the 7-day test product usage period. The questions and statistical summaries of the results of the pre-test questionnaire and the post-test questionnaire for Example 4 are set forth in Tables 5-7.

Example 4A: Symptom Improvement

Participants used the test product according to the above instructions detailed in Example 4 over the test period.

Participants were asked in both the pre-test and in the post-test questionnaires to rate the average severity of participant's skin on a scale from 0 to 10 for each of the following four symptoms: flaking, dryness or roughness, itch, and redness, when thinking of participant's skin over the last 3 days or nights, a score of 0=no symptom, 10=severe symptom: (e.g., 0=no itching, 10=severe itching). Responses for each prompt were averaged to provide a score for each prompt within each respective group of participants. The resulting score from the pre-test questionnaire provided a baseline score. The resulting score from the post-test questionnaire provided a final score. The percent (%) improvement from the baseline score to the final score was then calculated. Results are shown in Table 5, below.

TABLE 5

Summary of Percent Improvement of Symptoms of Flaking, Dryness or Roughness, Itch, and Redness after 7-Day Test Period

| | Test 1 | | Test 2 | | |
|---|---|---|---|---|---|
| | Example 4 Group | | | | |
| | 1 | 2 | 3 | 4 | 5 |
| | Number of Participants | | | | |
| | 11 | 12 | 14 | 14 | 14 |
| | Example 4 Test Product | | | | |
| | Comparative Composition 2 | Test Composition 1 | Comparative Composition 1 | Comparative Composition 3 | Test Composition 1 |
| Contains *Centella asiatica* extract | — | x | — | x | x |
| Contains Avena (oat) extract | x | x | — | — | x |
| Contains Ceramide(s) | x | x | — | — | x |
| Symptom | | | | | |
| Flaking | 51% | 51% | 51% | 66% | 70% |
| Dryness or Roughness | 41% | 58% | 52% | 62% | 56% |
| Itch | 53% | 54% | 56% | 62% | 70% |
| Redness | 35% | 48% | 48% | 63% | 71% |

As shown in Table 5, participants using the composition having only *Centella asiatica* extract (Comparative Composition 3) reported generally good scores for reducing symptoms when compared with compositions according to the present disclosure. Also shown in Table 5, participants using *Centella asiatica* extract, oats, and ceramides (Test Composition 1) also reported generally good scores compared to compositions having only *Avena* (oat) extract and ceramides (Comparative Composition 2, in test 1), or the chassis alone (Comparative Composition 1, in test 2). Thus, the results indicate that *Centella asiatica* extract alone may be sufficient in providing relief of symptoms associated with challenged skin, however, compositions according to the present disclosure may be much better in providing relief of symptoms associated with challenged skin.

Example 4B: Consumer Acceptance Ratings

Participants used the test product according to the above instructions detailed in Example 4 over the test period. Participants were asked in the post-test questionnaire a series of prompts (reproduced in Table 4, below) and to select a score (100=excellent; 75=very good; 50=good; 25=fair; 0=poor) as to their opinion in response of each prompt. Responses for each prompt were averaged to provide a resulting score prompt per each respective group of participants. Results are shown in Table 6, below.

TABLE 6

Summary of Consumer Acceptance Ratings after 7-Day Test Period

| | Test 1 | | Test 2 | | |
|---|---|---|---|---|---|
| | | | Example 4 Group | | |
| | 1 | 2 | 3 | 4 | 5 |
| | | | Number of Participants | | |
| | 11 | 12 | 14 | 14 | 14 |
| | | | Example 4 Test Product | | |
| | Comparative Composition 2 | Test Composition 1 | Comparative Composition 1 | Comparative Composition 3 | Test Composition 1 |
| Contains *Centella asiatica* extract | — | x | — | x | x |
| Contains Avena (oat) extract | x | x | — | — | x |
| Contains Ceramides | x | x | — | — | x |
| Prompt: Considering everything about the Eczema Cream test product/test cream, please indicate the one word or phrase which best describes your overall opinion of this product. + | | | | | |
| Overall Opinion of Product | 52 | 73** | 79 | 80 | 75 |
| Prompt: Please rate the eczema cream test product/test cream on the following characteristics: ++ | | | | | |
| Reducing itching | 59 | 65 | 73 | 71 | 77 |
| Allows Me to Forget About My Eczema/Skin Problems +++ | 43 | 58 | 52 | 66* | 64* |
| Being Easy to Spread on Skin | 73 | 85* | 86 | 88 | 86 |
| Enjoyable to Use | 48 | 77** | 77 | 82 | 73 |
| Improves Overall Appearance of My Skin | 57 | 75* | 68 | 70 | 68 |
| Leaving Skin Feeling Moisturized | 57 | 79** | 79 | 71 | 73 |
| Leaving Skin Feeling Soothed | 61 | 77* | 75 | 77 | 75 |

TABLE 6-continued

Summary of Consumer Acceptance Ratings after 7-Day Test Period

| | Test | | | | |
|---|---|---|---|---|---|
| | 1 | | 2 | | |
| | Example 4 Group | | | | |
| | 1 | 2 | 3 | 4 | 5 |
| | Number of Participants | | | | |
| | 11 | 12 | 14 | 14 | 14 |
| | Example 4 Test Product | | | | |
| | Comparative Composition 2 | Test Composition 1 | Comparative Composition 1 | Comparative Composition 3 | Test Composition 1 |
| Leaving Skin Soft and Smooth | 52 | 83** | 77 | 75 | 79 |
| No Need to Reapply Product/ Lasts All Day | 34 | 56** | 57 | 59 | 55 |
| Not Irritating Skin | 70 | 83* | 79 | 80 | 88 |
| Not Leaving Skin Feeling Greasy/Oily | 52 | 81** | 84 | 84 | 82 |

+ In Test 1, stated "eczema cream product". In Test 2, stated "test cream".
++ In Test 1, stated "eczema cream test product". In Test 2, stated "test cream"
+++ In Test 1, stated "eczema". In Test 2, stated "skin problems".
*The resulting score is statistically significant at an 80% confidence interval vs. the resulting score of Comparative Composition 2 (Test 1) or vs. Comparative Composition 1 (Test 2).
**The resulting score is statistically significant at a 90% confidence interval vs. the resulting score of Comparative Composition 2 (Test 1) or vs. Comparative Composition 1 (Test 2).

As shown in Table 6, participants using the composition having only *Avena* (oat) extract and ceramides (Comparative Composition 2) reported a lower consumer score for reducing symptoms (itch) (as per every other prompt) than compositions according to the present disclosure and thus may be inferior to consumers in goodness of providing relief of symptoms. Compositions having only *Centella asiatica* extract (Comparative Composition 3) reported a lower consumer score for reducing symptoms (itch) when compared with compositions according to the present disclosure, however, the score for reducing symptoms (itch) was still generally a good score and the composition further scored well in many of the other prompts, thus indicating that *Centella asiatica* extract alone may be sufficient in providing relief of symptoms associated with challenged skin, however, compositions according to the present disclosure may be much better in providing relief of symptoms associated with challenged skin.

Example 4C: Potential for Irritation

It is known that many *Avena* (oat) extracts maintain low irritation profiles, and that ceramides provide hydration benefits to the skin assisting in alleviating irritation. However, the addition of certain ingredients to compositions containing *Avena* (oat) extracts and ceramides may negatively affect the irritation profiles and/or the stinging or burning profiles of the newly formed composition. Test Composition 1 and Comparative Compositions 1-3 were tested to compare whether the addition of *Centella asiatica* extract according to the present disclosure affected irritation, stinging, and/or burning when added to a composition including *Avena* (oat) extracts and ceramides.

Participants used the test product according to the above instructions detailed in Example 4 over the test period. Participants were asked in the post-test questionnaire the following question: "[did] the eczema cream (Test 1)/test cream (Test 2) cause any of the following negative skin effects?" Participants then selected either "yes" or "no" as to each of the following skin effects: stinging, burning, redness, itching, other. The percentage of each of Groups 1-5 of participants who responded "yes" to either prompt of stinging or burning is shown in Table 7, below. The percentage of each of Groups 1-5 of participants who responded "yes" to any of the skin effects is shown in Table 5, below, under "any irritation".

TABLE 7

Summary of Percentage of Participants Experiencing Stinging, Burning, Redness, Itching, or Other Negative Skin Effects

| | Test 1 | | | Test 2 | |
|---|---|---|---|---|---|
| | Group | | | | |
| | 1 | 2 | 3 | 4 | 5 |
| | Number of Participants | | | | |
| | 11 | 12 | 14 | 14 | 14 |
| | Example 4 Test Product | | | | |
| | Comparative Composition 2 | Test Composition 1 | Comparative Composition 1 | Comparative Composition 3 | Test Composition 1 |
| Contains *Centella asiatica* extract | — | x | — | x | x |
| Contains *Avena* (oat) extract | x | x | — | — | x |
| Contains Ceramides | x | x | — | — | x |
| Symptom | | | | | |
| Stinging or Burning | 9% | 8% | 29% | 21% | 7% |
| Any Irritation (stinging, burning, redness, itching, or other) | 9% | 8% | 29% | 21% | 14% |

The data in Table 7 demonstrates that compositions having only *Centella asiatica* extract (Comparative Composition 3) may not be sufficient for mitigating instances of irritation of the skin (21% instances of irritation) and thus may be insufficient in providing both relief of symptoms and being non-irritating. Surprisingly, when *Avena* (oat) extract and ceramides were added to *Centella asiatica* extract, the resulting composition resulted in scoring a percentage of instances of irritation nearly the same as the composition having only *Avena* (oat) extract and ceramides and much better than *Centella asiatica* extract alone. Applicant has demonstrated that compositions of the present disclosure may be superior in mitigating instances of irritation of the skin.

Example 5: Signature Free Method of Querying Perturbagens Using Connectivity Mapping to Test Similarity Among Different Varieties of *Centella asiatica* Extracts Data analysis was run according to the Signature Free Method of Querying Perturbagens Using Connectivity Mapping to Test Similarity Among Different Varieties of Perturbagens as described herein. A query was made using *Centella asiatica* Selected Triterpenes (CAST) supplied by Indena (Milan, Italy). Each of the perturbagens was then ranked according to its distance from *Centella asiatica* Selected Triterpenes (CAST). The resulting matrix was then filtered to show only versions of *Centella asiatica* extracts and was used to determine the similarity or the dissimilarity between the various *Centella asiatica* extracts that were part of the database and *Centella asiatica* Selected Triterpenes (CAST). Fisher Discriminant Analysis was used.

Eight different varieties of *Centella asiatica* extracts from different suppliers that existed on the C-map database were compared to *Centella asiatica* Selected Triterpenes (CAST). Each perturbagen comprised different concentrations of triterpenes as shown in the material descriptions below Table 8. The resulting similarity (distance) matrix is summarized below in Table 8.

TABLE 8

Similarity (Distance) Matrix of Various *Centella Asiatica* Extracts from *Centella Asiatica* Selected Triterpenes (CAST)

| Perturbagen Name | Concentration Tested (wt. %) | Score |
|---|---|---|
| *Centella Asiatica* Selected Triterpenes (CAST) | 0.001% | 1.000 |
| Madecassic acid | 0.01% | 0.770 |
| Titrated Extract of *Centella Asiatica* (TECA) | 0.01% | 0.495 |
| CENTELLIN ® CG | 0.001% | 0.280 |
| CENTEVITA ™ | 0.001% | 0.236 |
| CENTEVITA ™ | 10% | 0.227 |
| CENTELLIN ® CG | 0.01% | 0.204 |
| CENTEVITA ™ | 0.01% | 0.203 |
| CENTELLIN ® CG | 0.01% | 0.165 |
| CENTELLIN ® CG | 10% | 0.114 |
| COSMELENE ® OF *CENTELLA* | 0.01% | 0.018 |
| Madecassoside | 0.01% | −0.031 |

TABLE 8-continued

Similarity (Distance) Matrix of Various *Centella Asiatica* Extracts from *Centella Asiatica* Selected Triterpenes (CAST)

| Perturbagen Name | Concentration Tested (wt. %) | Score |
|---|---|---|
| *CENTELLA* STEMS GX ™ | 0.01% | −0.123 |
| CENTECELL ™ | 0.001% | −0.228 |

*Centella Asiatica* Selected Triterpenes (CAST) supplied by Indena (Milan, Italy). HPLC content: ≥36.0% ≤ 44.0% of asiaticoside, ≥56% ≤ 64% of genins as a sum of asiatic acid and madecassic acid.
Madecassic acid (100%): molecular formula: $C_{30}H_{48}O_6$.
Titrated Extract of *Centella Asiatica* (TECA ®) as supplied by SEPPIC (Paris, France). INCI Name: Asiaticoside (and) Madecassic Acid (and) Asiatic Acid. INCI: Asiaticoside (and) Madecassic Acid (and) Asiatic Acid. HPLC: ≥15% ≤ 25% of asiatic acid; ≥25% ≤ 50% of madecassic acid; ≥25% ≤ 50% of O-6-Deoxy-.alpha.-L-mannopyranosyl-(1.−>.4)-O-.beta.-D-glucopyranosyl-(1.−>.6)-.beta-Dglucopyranosyl (2.alpha.,3.beta.,4.alpha.) - 2,3,23-trihydroxyurs-12-en-28-oate.
CENTELLIN ® CG (*Centella asiatica* extract CG) supplied by Sabinsa Cosmetics (East Windsor, New Jersey, U.S.A.) ≥40% ≤ 50% total triterpene saponins. INCI: *Centella Asiatica* Extract.
CENTEVITA ™ supplied by Indena (Milan, Italy). HPLC content: ≥45.0% of the sum of asiaticoside, madecassoside, asiatic acid and madecassic acid.
COSMELENE ® OF *CENTELLA* supplied by Greentech (Saint Beauzire, France). INCI: butylene glycol, *Centella asiatica* extract. Asiaticoside-madecassoside 0.8-1.2%; butylene glycol ≥90%; heavy metals <10 ppm.
Madecassoside supplied by Indena (Milan, Italy). HPLC content: ≥95.0% of madecassoside and terminoloside.
*CENTELLA* STEMS GX ™ supplied by IRB Cosmetics by Sederma S.A. (Le Perray en Yvelines, France). 80% Glycerin, 20% of *Centella asiatica* Meristem Cell Culture and Xantham Gum.
CENTECELL ™ supplied by IRB Cosmetics by Sederma S.A. (Sederma S.A. (Le Perray en Yvelines, France). Includes phenylpropanoids: 4-malonil-3,5-dicaffeoylquinic acid, 3,5-dicaffeoylquinic acid, 1,3,5-tricaffeoylquinic acid, phytosterols, amino acids, polysaccharides. INCI: Glycerin (and) *Centella Asiatica* Extract (and) Xanthan Gum.

The results of Table 8 suggest that among the different varieties of *Centella asiatica* extracts tested, madecassic acid and TECA, an extract containing asiaticoside and madecassic acid and asiatic acid, ranked closer in similarity score in its effect on gene expression in tert keratinocytes to CAST than any of the other varieties of *Centella asiatica* extract tested. The array of similarity scores shown in Table 8 indicates that not all varieties of *Centella asiatica* extract have the same functional activity and thus selecting a particular *Centella asiatica* extract to provide the aforementioned benefits of the present disclosure is needed.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A topical skincare composition comprising:
   from about 0.0001% to about 1.5% of a *Centella asiatica* extract consisting essentially of from about 20% to about 60% by weight of the *Centella asiatica* extract of asiaticoside and from about 40% to about 80% by weight of the *Centella asiatica* extract of a mixture of asiatic acid and madecassic acid;
   from about 0.0001% to about 10% of an *Avena* (oat) extract;
   from about 0.001% to about 1% a ceramide;
   from about 0.1% to about 15% by weight of the composition of a lipid bilayer structurant;
   at least about 0.01% by weight of the composition of a preservative; and
   from about 50% to about 98% of a dermatologically acceptable carrier, wherein the dermatologically acceptable carrier is an oil-in-water emulsion.

2. The topical skincare composition according to claim 1, wherein the *Avena* (oat) extract comprises an *Avena sativa* (oat) extract.

3. The topical skincare composition according to claim 1, wherein the *Avena* (oat) extract is selected from the group consisting of *Avena sativa* (oat) kernel extract, *Avena sativa* (oat) oil, colloidal oatmeal, and mixtures thereof.

4. The topical skincare composition according to claim 1, wherein the topical skincare composition is substantially free of a steroid.

5. The topical skincare composition according to claim 1, wherein the composition has a viscosity of from about 30,000 cP to about 300,000 cP, when measured according to the Viscosity Test Method described herein.

6. A topical skincare composition capable of alleviating symptoms associated with eczematous dermatitis, contact dermatitis, atopic dermatitis, and/or psoriasis, the topical skincare composition comprising from about 0.0001% to about 1.5% a *Centella asiatica* extract consisting essentially of from about 20% to about 60% by weight of the *Centella asiatica* extract of asiaticoside and from about 40% to about 80% by weight of the *Centella asiatica* extract of a mixture of asiatic acid and madecassic acid, from about 0.0001% to about 10% *Avena sativa* (oat) kernel extract and *Avena sativa* (oat) oil, from about 0.001% to about 1% a ceramide, from about 0.1% to about 15% batyl alcohol, at least about 0.01% by weight of caprylyl glycol and 1,2-hexanediol, and from about 50% to about 98% of a dermatologically acceptable carrier.

7. The topical skincare composition according to claim 3, wherein the *Avena* (oat) extract is a mixture of *Avena sativa* (oat) kernel extract and *Avena sativa* (oat) oil.

8. The topical skincare composition according to claim 7, wherein the concentration of *Avena sativa* (oat) oil is less than or equal to about 0.25%.

\* \* \* \* \*